(12) United States Patent
Jarvi et al.

(10) Patent No.: US 7,498,439 B2
(45) Date of Patent: Mar. 3, 2009

(54) SYNTHESIS OF HETEROARYL ACETAMIDES FROM REACTION MIXTURES HAVING REDUCED WATER CONTENT

(75) Inventors: Esa Jarvi, Ballwin, MO (US); Douglas C. Miller, University City, MO (US); Frank W. Moser, Arnold, MO (US); Robert E. Halvachs, Belleville, IL (US)

(73) Assignee: Mallinckrodt Inc., Hazelwood, MO (US)

( * ) Notice: Subject to any disclaimer, the term of this patent is extended or adjusted under 35 U.S.C. 154(b) by 0 days.

(21) Appl. No.: 10/594,486

(22) PCT Filed: Jun. 3, 2005

(86) PCT No.: PCT/US2005/019810

§ 371 (c)(1),
(2), (4) Date: Sep. 27, 2006

(87) PCT Pub. No.: WO2006/007289

PCT Pub. Date: Jan. 19, 2006

(65) Prior Publication Data

US 2007/0213537 A1    Sep. 13, 2007

(51) Int. Cl.
*C07D 235/06* (2006.01)
*C07D 403/02* (2006.01)
*C07D 471/04* (2006.01)
*C07D 491/04* (2006.01)

(52) U.S. Cl. ............... 546/118; 548/303.1; 548/309
(58) Field of Classification Search ............... 546/118; 548/303.1, 309
See application file for complete search history.

(56) References Cited

U.S. PATENT DOCUMENTS

| 4,794,185 A | 12/1988 | Rossey et al. |
| 5,512,590 A | 4/1996 | George et al. |
| 6,407,240 B1 | 6/2002 | Labriola |

FOREIGN PATENT DOCUMENTS

| EP | 1 172 364 | 1/2002 |
| FR | 2700546 | 7/1994 |
| FR | 2741073 | 5/1997 |
| WO | WO 2004/058758 | 7/2004 |

OTHER PUBLICATIONS

March, Adv. Org. Chem. 2nd Ed. (1977), p. 402.*
March, Adv. Org. Chem. 2$^{nd}$ Ed. (1977), p. 402.

* cited by examiner

Primary Examiner—Taofiq A Solola

(57) ABSTRACT

An improved process for the preparation of a heteroaryl acetamide from a heteroaryl α-hydroxyacetamide is provided. The process comprises directly hydrogenating the heteroaryl α-hydroxyacetamide in the presence of a strong acid, a halide and a catalyst wherein the molar ratio of the starting heteroaryl α-hydroxyacetamide to water at the initiation of hydrogenolysis is at least about 2:1. In one embodiment, the heteroaryl acetamide is zolpidem and the heteroaryl α-hydroxyacetamide is α-hydroxyzolpidem.

23 Claims, No Drawings

SYNTHESIS OF HETEROARYL ACETAMIDES FROM REACTION MIXTURES HAVING REDUCED WATER CONTENT

BACKGROUND OF THE INVENTION

The present application is generally directed to a process for the synthesis of heteroaryl acetamides.

Various processes for the preparation of heteroaryl acetamides have been proposed. In general, they differ in the procedure used for the introduction of the acetamide chain.

In U.S. Pat. No. 4,794,185, Rossey et al. disclose a process of preparing an imidazopyridine acetamide by reacting an imidazopyridine with a dialkoxyalkylamide to produce an imidazopyridine α-hydroxyacetamide intermediate. The intermediate is then converted to an α-chloroacetamide and subsequently reduced to produce the desired imidazopyridine acetamide.

SUMMARY OF THE INVENTION

Among the various aspects of the present invention is a process for converting heteroaryl α-hydroxyacetamides directly to the corresponding heteroaryl acetamides. In one embodiment, the process comprises hydrogenating the heteroaryl α-hydroxyacetamide in the presence of a strong acid, a halide and a hydrogenation catalyst wherein the molar ratio of the starting heteroaryl α-hydroxyacetamide to water at the initiation of hydrogenolysis is at least about 2:1.

The present invention is further directed to a process for converting imidazopyridine α-hydroxyacetamides directly to the corresponding imidazopyridine acetamides. In this embodiment, an imidazopyridine α-hydroxyacetamide is hydrogenated in the presence of a strong acid, a halide and a hydrogenation catalyst wherein the molar ratio of the starting heteroaryl α-hydroxyacetamide to water at the initiation of hydrogenolysis is at least about 2:1.

In another embodiment, α-hydroxy zolpidem is hydrogenated in the presence of a strong acid, a halide and a hydrogenation catalyst to produce zolpidem wherein the molar ratio of the starting α-hydroxy zolpidem to water at the initiation of hydrogenation is at least about 2:1.

DETAILED DESCRIPTION

Among the various aspects of the invention is a process for preparing heteroaryl acetamides which are biologically active, by directly hydrogenating heteroaryl α-hydroxyacetamides in the presence of a strong acid, a halide, and a catalyst.

In one embodiment, the starting heteroaryl α-hydroxyacetamide is represented by Formula 1 (or a salt thereof) and the product heteroaryl acetamide is represented by Formula 1A (or a salt thereof).

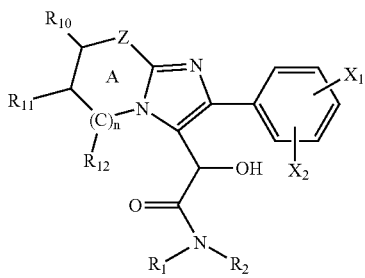

Formula 1

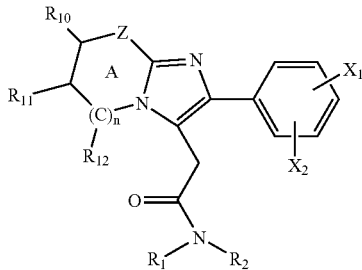

Formula 1A wherein

Z is O, $NR_{20}$ or $CR_{21}$;

$X_1$ and $X_2$ are independently selected from the group consisting of hydrogen, halogen, $C_{1-4}$ alkoxy, $C_{1-6}$ alkyl, $CF_3$ and $CH_3SO_2$;

$R_1$ and $R_2$ are independently hydrogen or $C_{1-5}$ alkyl;

$R_{10}$ is hydrogen, halogen, $C_{1-4}$ alkyl, or a member of a fused ring wherein the fused ring is (i) a substituted or unsubstituted, saturated or unsaturated, five or six-membered, heterocyclic or carbocyclic ring fused to the A ring comprising $R_{10}$, the carbon atom to which $R_{10}$ is attached, $R_{20}$, and the nitrogen atom to which $R_{20}$ is attached, or (ii) a six-membered, aromatic, carbocyclic ring fused to the A ring comprising $R_{10}$, $R_{11}$, and the carbon atoms to which $R_{10}$ and $R_{11}$, are attached, optionally substituted with Y at a substitutable position thereof;

$R_{11}$ is hydrogen, halogen, $C_{1-4}$ alkyl, or a member of a fused ring wherein the fused ring is (i) a six-membered, aromatic, carbocyclic ring fused to the A ring comprising $R_{10}$, $R_{11}$, and the carbon atoms to which $R_{10}$ and $R_{11}$ are attached, optionally substituted with Y at a substitutable position thereof, or (ii) a six-membered, aromatic, carbocyclic ring fused to the A ring comprising $R_{11}$, $R_{12}$, and the carbon atoms to which $R_{11}$ and $R_{12}$ are attached, optionally substituted with Y at a substitutable position thereof;

$R_{12}$, if present, is hydrogen, halogen, $C_{1-4}$ alkyl, or a member of a fused ring wherein the fused ring is (i) a six-membered, aromatic, carbocyclic ring fused to the A ring comprising $R_{11}$, $R_{12}$, and the carbon atoms to which $R_{11}$ and $R_{12}$ are attached, optionally substituted with Y at a substitutable position thereof;

$R_{20}$ is $C_{1-4}$ alkyl or a member of a fused ring wherein the fused ring is a substituted or unsubstituted, saturated or unsaturated, five or six-membered, heterocyclic or carbocyclic ring fused to the A ring comprising $R_{10}$, the carbon atom to which $R_{10}$ is attached, $R_{20}$, and the nitrogen atom to which $R_{20}$ is attached;

$R_{21}$ is hydrogen, halogen or $C_{1-4}$ alkyl;

n is 0 or 1;

each Y is independently hydrogen, halogen or $C_{1-4}$ alkyl; and when Z is $CR_{21}$, the A ring is aromatic.

In a further embodiment, the starting material and product of the process of the present invention have the structures of Formulae 1 and 1A, respectively, wherein Z is —$NR_{20}$, n is zero, $R_{20}$ and $R_{10}$ together with the atoms to which they are attached define a five-membered heterocyclic ring fused to the A ring, and $R_{10}$ and $R_{11}$ together with the atoms to which they are attached define a six-membered, aromatic, carbocyclic ring fused to the A ring. In this embodiment, for example, the starting material and product may correspond to Formulae 2 (or a salt thereof) and 2A (or a salt thereof), respectively,

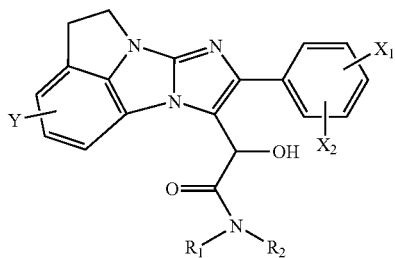

Formula 2

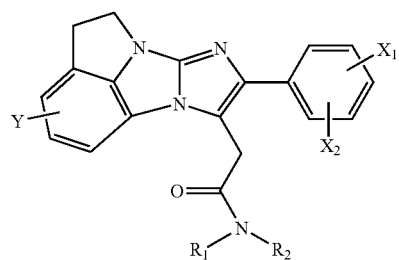

Formula 2A wherein $R_1$, $R_2$, $X_1$, $X_2$ and Y are as previously defined. In one preferred embodiment when the starting material and product correspond to Formulae 2 and 2A, $X_1$ and $X_2$ are independently hydrogen or halogen, $R_1$ and $R_2$ are independently hydrogen or $C_{1-5}$ alkyl, and Y is hydrogen, halogen or $C_{1-4}$ alkyl.

In another embodiment, the starting material and product of the process of the present invention have the structures of Formulae 1 and 1A wherein Z is —$NR_{20}$, n is zero, $R_{20}$ and $R_{10}$ together with the atoms to which they are attached define a six-membered heterocyclic ring fused to the A ring, and $R_{10}$ and $R_{11}$ together with the atoms to which they are attached define a six-membered, aromatic carbocyclic ring fused to the A ring. In this embodiment, for example, the starting material and product may correspond to Formulae 3 (or a salt thereof) and 3A (or a salt thereof), respectively,

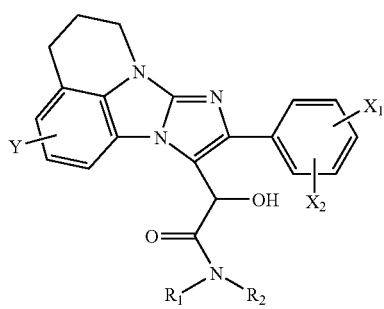

Formula 3

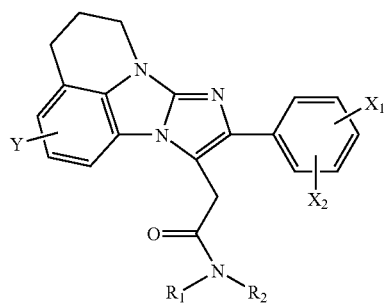

Formula 3A wherein $R_1$, $R_2$, $X_1$, $X_2$ and Y are as previously defined. In one preferred embodiment when the starting material and product correspond to Formulae 3 and 3A, $X_1$ and $X_2$ are independently hydrogen or halogen, $R_1$ and $R_2$ are independently hydrogen or $C_{1-5}$ alkyl and Y is hydrogen, halogen or $C_{1-4}$ alkyl.

In yet another embodiment, the starting material and product of the process of the present invention have the structures of Formulae 1 and 1A wherein Z is O, n is zero, $R_{10}$ and $R_{11}$ together with the atoms to which they are attached define a six-membered, aromatic carbocyclic ring fused to the A ring. In this embodiment, for example, the starting material and product may correspond to Formulae 4 (or a salt thereof) and 4A (or a salt thereof), respectively,

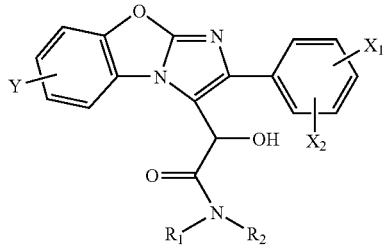

Formula 4

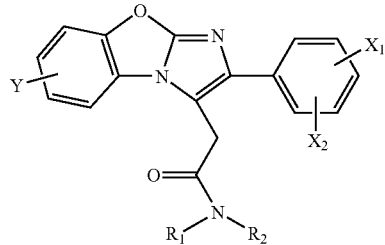

Formula 4A wherein $R_1$, $R_2$, $X_1$, $X_2$ and Y are as previously defined. In one preferred embodiment when the starting material and product correspond to Formulae 4 and 4A, $X_1$ and $X_2$ are independently hydrogen or halogen, $R_1$ and $R_2$ are independently hydrogen or $C_{1-5}$ alkyl and Y is hydrogen, halogen or $C_{1-4}$ alkyl.

In still another embodiment, the starting material and product of the process of the present invention have the structures of Formulae 1 and 1A wherein Z is $NR_{20}$, n is zero, $R_{10}$ and $R_{11}$ together with the atoms to which they are attached define a six-membered, aromatic carbocyclic ring fused to the A ring. In this embodiment, for example, the starting material and product may correspond to Formulae 5 (or a salt thereof) and 5A (or a salt thereof), respectively,

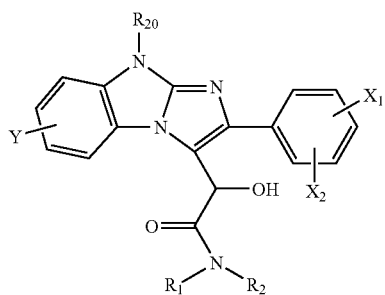

Formula 5

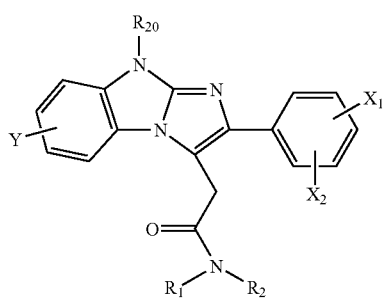

Formula 5A wherein $R_1$, $R_2$, $X_1$, $X_2$ and Y are as previously defined. In one preferred embodiment when the starting material and product correspond to Formulae 5 and 5A, $X_1$ and $X_2$ are independently hydrogen or halogen, $R_1$ and $R_2$ are independently hydrogen or $C_{1-5}$ alkyl and Y is hydrogen, halogen or $C_{1-4}$ alkyl.

In a further embodiment, the starting material and product of the process of the present invention have the structures of Formulae 1 and 1A wherein Z is $CR_{21}$, $R_{10}$, $R_{11}$, $R_{12}$, and $R_{21}$ are independently hydrogen, halogen or $C_{1-4}$ alkyl and n is 1. In this embodiment, for example, the starting material, a heteroaryl α-hydroxyacetamide, and product, a heteroaryl acetamide, may correspond to Formulae 6 (or a salt thereof) and 6A (or a salt thereof), respectively,

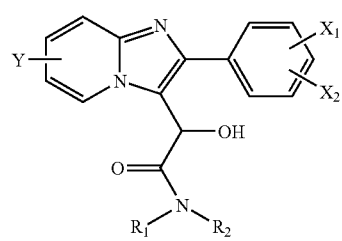

Formula 6

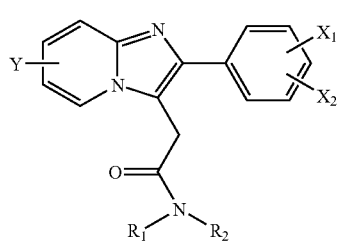

Formula 6A wherein
Y is hydrogen, halogen or $C_{1-4}$ alkyl;
$X_1$ and $X_2$ are independently selected from the group consisting of hydrogen, halogen, $C_{1-4}$ alkoxy, $C_{1-6}$ alkyl, $CF_3$ and $CH_3SO_2$; and
$R_1$ and $R_2$ are independently hydrogen or $C_{1-5}$ alkyl.

In another embodiment, the starting imidazopyridine α-hydroxyacetamide is represented by Formula 7 (or a salt thereof) and the imidazopyridine acetamide product is represented by Formula 7A (or a salt thereof),

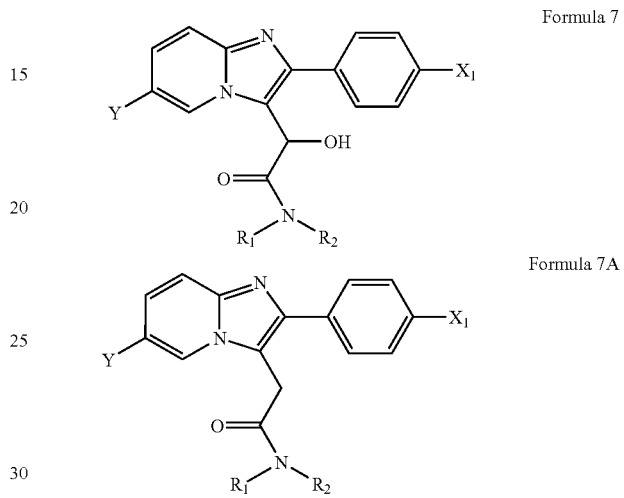

Formula 7

Formula 7A

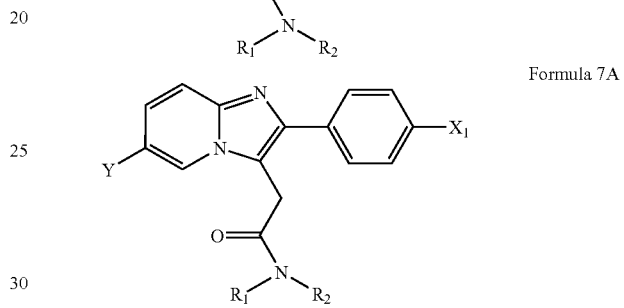

wherein Y, $X_1$, $R_1$ and $R_2$ are $C_{1-4}$ alkyl. When each of Y, $X_1$, $R_1$ and $R_2$ are methyl, the compound of Formula 7 is α-hydroxyzolpidem (AHZ) and the compound of Formula 7A is zolpidem.

In this context, a salt of Formula 1-7 or 1A-7A is a recovered product wherein the salt has an associated counterion. When compounds of Formulae 1-7 or 1A-7A are in solution and in an ionic form, this is a solution of a salt. When the compounds of Formulae 1-7 or 1A-7A are ions either as a solid or in solution, they are in the salt form. Whether the compounds corresponding to Formulae 1-7 or Formulae 1A-7A are in an ionic form or free base form depends on the pH of the compound's environment. If the pH is equal to the $pK_a$ of the protonated form, 50% of the molecules are protonated and the other 50% are unprotonated. Accordingly, if the pH is less than the $pK_a$ of the protonated form of Formulae 1-7 or 1A-7A, then the salt form will be the predominant form, however, if the pH is greater than the pKa of the protonated form of Formulae 1-7 or 1A-7A, then the free base form will be the predominant form.

In one embodiment, the starting heteroaryl α-hydroxyacetamide is a salt of one of Formulae 1-7 and the heteroaryl acetamide product is either the corresponding salt of one of Formulae 1A-7A or the free base of one of Formulae 1A-7A, depending on the pH. The negatively charged counterion of these salts may be derived from an acid which has a $pK_a$ less than the $pK_a$ of the protonated form of the starting heteroaryl α-hydroxyacetamide or product heteroaryl acetamide. Exemplary counterions are chloride, bromide, iodide, sulfate, nitrate, acetate and the like.

Alternatively, the starting heteroaryl α-hydroxyacetamide is a free base corresponding to one of Formulae 1-7 and the heteroaryl acetamide product is a salt or a free base corresponding to one of Formula 1A-7A. In general, the compounds of Formulae 1A-7A will react with a composition that is a stronger acid than the conjugate acid of the heteroaryl acetamide of Formulae 1A-7A. Stated another way, a compound with a $pK_a$ lower than the $pK_a$ of the protonated heteroaryl acetamide of Formulae 1A-7A will react to form salts. A presently preferred salt is the hemitartrate salt of zolpidem (i.e., the compound of Formula 7A wherein each of Y, $X_1$, $R_1$ and $R_2$ are methyl).

The heteroaryl α-hydroxyacetamides of Formulae 1-5 may be prepared by reaction of the appropriate fused ring imidazo derivative with glyoxylic acid to produce an α-hydroxy acid which is subsequently acetylated, transformed into the α-acetoxy acetamide via an imidazolide and de-acetylated to produce an α-hydroxy acetamide. This process is described in more detail in U.S. Pat. No. 4,675,323 and FR 2593179.

The imidazopyridine α-hydroxyacetamides of Formulae 2-4 and 6-7, generally, may be prepared by reaction of the appropriate imidazo derivative with N,N-dimethyl-2,2-dimethoxyacetamide or N,N-dimethyl-2,2-diethoxyacetamide to produce the imidazo α-hydroxyacetamide used as the starting material in the present invention. This process is described in more detail in U.S. Pat. No. 4,794,185, U.S. Pat. No. 5,512,590, WO 00/08021, FR 2700546 and FR 2741073.

In general, each of the products, i.e., the compounds of Formulae 1A-7A may be formed by the direct hydrogenation of the compounds of Formulae 1-7 respectively, in the presence of hydrogen gas, a strong acid, a halide and a hydrogenation catalyst.

The hydrogenation catalyst is typically a solid catalyst in whatever form is suitable and effective for achieving the hydrogenation reactions of the invention. In one embodiment, the catalyst is a precious metal catalyst. For example, the catalyst may be a platinum, palladium, ruthenium, osmium, iridium, or rhodium catalyst, or a combination thereof. In another embodiment, the catalyst is a platinum group metal catalyst. For example, the catalyst may be a palladium or platinum catalyst. In yet another embodiment, preferably the catalyst is a palladium catalyst.

The catalyst may be supported on carbon, barium sulfate, alumina, strontium carbonate, calcium carbonate and the like. Thus, for example, catalysts include palladium on barium sulfate, palladium on carbon, palladium on alumina, palladium on strontium carbonate, palladium on barium carbonate, palladium on calcium carbonate, and the like. In a further embodiment of the invention, preferably the palladium catalysts are palladium on barium sulfate and palladium on carbon, particularly palladium on carbon.

The halide used in the process may be a fluoride, chloride, bromide, or iodide ion. In one embodiment, preferably, the halide used in the process is chloride or bromide. In a further embodiment, preferably the halide is bromide.

The halide source may be any salt that does not interfere with the purification steps. For example, the halide source may be an alkali metal halide, alkaline earth metal halide, transition metal halide, halide salt of an organic cation, or the like. In one embodiment, the halide source is an alkali metal bromide, alkali metal chloride, alkaline earth metal bromide, alkaline earth metal chloride, transition metal bromide, transition metal chloride, bromide or chloride salt of an organic cation, or the like. In another embodiment, the halide source is a bromide salt where the cation does not interfere with the purification of the compounds of formulae 1A-7A. In one particular embodiment, the halide source is LiBr, NaBr, KBr, $MgBr_2$, $CaBr_2$ or $NH_4Br$. In yet a further embodiment, the halide source is LiBr or KBr.

In general, the strong acid or mixture of strong acids preferably has an approximate pKa (relative to water) of about −9 or less. In addition, after the starting material of Formulae 1-7, the strong acid, the halide, the catalyst and the solvent are charged in the reaction vessel, the reaction mixture preferably has a chloride or bromide concentration of about $2.1 \times 10^{-5}$ M to $1.8 \times 10^4$ M or less. Experimental evidence to-date generally shows that a greater halide concentration negatively impacts the yield of the reaction. In one embodiment of the invention, the strong acid is sulfuric acid, perchloric acid or a mixture of sulfuric and perchloric acids. In a further embodiment, the strong acid, preferably, is sulfuric acid. Without being bound by theory, the addition of the strong acid and halide to the reaction is believed to act to prevent side reactions such as reduction of the carbon-nitrogen double bonds.

The process may advantageously be carried out in carboxylic acid or alcoholic solvents. For example, the solvent may be methanol, ethanol, n-propanol, formic acid, acetic acid, propionic acid, and the like, or mixtures thereof. A presently preferred solvent is a carboxylic acid; preferably, the solvent is acetic acid.

The hydrogen source for the hydrogenation reaction is preferably hydrogen gas. The gas pressure will typically fall within the range of about 1 to 4 atmospheres. In one embodiment, the pressure range is from about 1 to 3 atmospheres. In a further embodiment of the invention, the pressure range is from about 2.0 to 2.8 atmospheres.

The reaction temperature of the process is not narrowly critical and typically falls within the range of about 40-100° C., preferably of about 50-80° C., and most preferably of about 70-75° C.

Generally, any reaction vessel which can withstand the pressure, temperature and corrosive properties of the reaction mixture can be used to carry out the process of the invention.

In one embodiment, the final product is obtained by filtration using techniques known in the art. In another embodiment, the method of filtration is pouring the reaction product into water and adding 20% sodium hydroxide or ammonium hydroxide to a pH of about 7-8 and filtering to give the desired product.

The amide group of the starting heteroaryl α-hydroxyacetamide and the amide group of the heteroaryl acetamide product may undesirably be hydrolyzed by water to form the corresponding carboxylic acid. For example, α-hydroxyzolpidem (AHZ) hydrolyzes to α-hydroxyzolpidic acid and zolipidem hydrolyzes to zolipidic acid.

The reaction mixture has several potential sources of water. For example, the halide source may contain water at a concentration of up to about 60 wt. %; the strong acid may contain water at a concentration of up to about 70 wt. % and certain commercially available catalysts, such as palladium on carbon catalyst, contain as much as 50% water. In addition, water is a product of the hydrogenation reaction and can further increase the water concentration in the reaction mixture; that is, hydrogenolysis of the starting heteroaryl α-hydroxyacetamide (i.e., composition of one of Formulae 1-7) to the corresponding heteroaryl acetamide product (i.e., a composition of one of Formulae 1A-7A) produces water as a by-product.

To minimize undesirable side reactions, the amount of the water in the reaction mixture is preferably minimized. In general, it is preferred that the molar ratio of the heteroaryl α-hydroxyacetamide to water in the reaction mixture at the initiation of hydrogenation reaction be greater than 2:1. More preferably, the molar ratio of the heteroaryl α-hydroxyacetamide to water in the reaction mixture at the initiation of hydrogenation reaction is greater than about 5:1. Even more preferably, the molar ratio of the heteroaryl α-hydroxyacetamide to water in the reaction mixture at the initiation of hydrogenation reaction is greater than about 10:1. Still more preferably, the molar ratio of the heteroaryl α-hydroxyacetamide to water in the reaction mixture at the initiation of hydrogenation reaction is greater than about 40:1. Still more preferably, the molar ratio of the heteroaryl α-hydroxyacetamide to water in the reaction mixture at the initiation of hydrogenation reaction is greater than about 75:1. Still more preferably, the molar ratio of the heteroaryl α-hydroxyacetamide to water in the reaction mixture at the initiation of hydrogenation reaction is greater than about 150:1.

To some extent, the water concentration in the reaction mixture may be controlled by forming a reaction mixture from relatively anhydrous starting materials. For example, commercially available palladium on carbon catalysts which typically carry about 50 wt. % water may be dried by a means known in the art, such as dessication, use of a drying agent (magnesium sulfate, molecular sieves, and the like), heating, vacuum drying, and the like to a water concentration of no more than 5 wt. %, preferably no more than 1 wt. %. Alternatively, other commercially available catalysts such as palladium on barium sulfate which typically carry less water may be selected.

When a palladium on carbon catalyst is selected, the water content of the reaction mixture at the initiation of the hydrogenolysis reaction is preferably less than about 2.5 wt. %; more preferably, less than about 2.0 wt. %; even more preferably, less than about 1.0 wt. %; and still more preferably, less than about 0.1 wt. %. In another embodiment, the water content of the reaction mixture is less than about 2.5 wt. % at the initiation of the hydrogenolysis reaction and maintained at this concentration until the hydrogenolysis reaction is stopped. Alternatively, the water content is less than about 2.0 wt. % at the initiation of the hydrogenolysis reaction and maintained at this concentration until the hydrogenolysis reaction is stopped. In yet another embodiment, the water content is less than about 1.0 wt. % at the initiation of the hydrogenolysis reaction and maintained at this concentration until the hydrogenolysis reaction is stopped. In still another embodiment, the water content of the reaction mixture is less than about 0.1 wt. % at the initiation of the hydrogenolysis reaction and maintained at this concentration until the hydrogenolysis reaction is stopped.

Water concentration in the reaction mixture may also be controlled by including a water scavenger in the reaction mixture. The water scavenger may be added separately from the other components of the reaction mixture or, alternatively, it may be pre-mixed with one of the other components and the mixture is then combined with the remainder. For example, the water scavenger may be combined with the strong acid to form an acid-scavenger mixture and this mixture is then combined with one or more of the other components (e.g., the catalyst, halide source or heteroaryl α-hydroxyacetamide substrate) to form the reaction mixture. By way of further example, the water scavenger may be combined with the halide source to form a halide source-scavenger mixture and this mixture is then combined with one or more of the other components (e.g., the catalyst, strong acid or heteroaryl α-hydroxyacetamide substrate) to form the reaction mixture. By way of further example, the water scavenger may be combined with heteroaryl α-hydroxyacetamide substrate to form a substrate-scavenger mixture and this mixture is then combined with one or more of the other components (e.g., the catalyst, strong acid or the halide source) to form the reaction mixture. By way of further example, the water scavenger may be combined with the catalyst to form a catalyst-scavenger mixture and this mixture is then combined with one or more of the other components (e.g., the strong acid, the halide source or heteroaryl α-hydroxyacetamide substrate) to form the reaction mixture. The concentration of water in the reaction mixture, prior to or at the initiation of the hydrogenolysis reaction may be influenced, therefore, by the amount of water scavenger added to the reaction mixture. For example, if less than one equivalent of the water scavenger per mole of water present is added to the reaction mixture, all of the water scavenger will be consumed and a portion of the water in the reaction mixture will be removed. Alternatively, if more than one equivalent of the water scavenger per mole of water present is added to the reaction mixture, all of the water will be removed and a portion of the water scavenger will be left to react with the water produced from the hydrogenolysis reaction.

In general, the water scavenger is preferably a composition which reacts with or absorbs the water. Exemplary compounds that react with water include carboxylic acid anhydrides, carboxylic acid chlorides, oleum and the like. Exemplary substances that absorb water include anhydrous inorganic salts that form hydrates (e.g., magnesium sulfate), molecular sieves and the like. Preferably, the water scavenger is a composition which, upon reaction with water, forms the solvent or one of the components of a solvent system (mixture). For example, when the solvent is acetic acid (or comprises acetic acid), the water scavenger is preferably acetic anhydride which reacts with water to form acetic acid; alternatively, other carboxylic acid anhydrides may be used.

In one exemplary embodiment, a water scavenger is added in a sufficient amount to remove the water associated with the reagents, especially the strong acid, the halide source and the catalyst. Generally, it is preferred that at least about 0.1 equivalents of the scavenger per mole of water present in the reaction mixture at the initiation of hydrogenolysis is added; more preferably, at least about 0.5 equivalents of the scavenger per mole of water present in the reaction mixture at the initiation of hydrogenolysis is added; even more preferably, at least about 0.9 equivalents of the scavenger per mole of water present in the reaction mixture at the initiation of hydrogenolysis is added. For example, in the conversion of α-hydroxyzolpidem to zolpidem, acetic acid is a preferred solvent and it is generally preferred that the reaction mixture contain at least 0.10 moles of acetic anhydride per mole of water present at the initiation of hydrogenolysis, and more preferably at least 0.9 moles of acetic anhydride per mole of water present at the initiation of hydrogenolysis to scavenge water.

In some embodiments, it may be preferred to include more than one equivalent of the water scavenger per mole of water present in the reaction mixture at the initiation of hydrogenolysis; an excess of water scavenger may thereby be used to scavenge water generated by the hydrogenolysis reaction. The excess equivalents of water scavenger may be present in the reaction mixture at a molar ratio of the initial heteroaryl α-hydroxyacetamide to excess water scavenger of at least about 20:1. Alternatively, the excess equivalents of water scavenger may be present in the reaction mixture at a molar ratio of the initial heteroaryl α-hydroxyacetamide to excess water scavenger of at least about 10:1. In a further embodiment, the excess equivalents of water scavenger may be present in the reaction mixture at a molar ratio of the initial heteroaryl α-hydroxyacetamide to excess water scavenger of at least about 5:1. In another embodiment, the excess equivalents of water scavenger may be present in the reaction mixture at a molar ratio of the initial heteroaryl α-hydroxyacetamide to excess water scavenger of at least about 1:1.

Advantageously, the yield of the conversion of α-hydroxy zolpidem to zolpidem using the process of the present invention was improved by addition of a water scavenging agent (e.g. acetic anhydride). This yield improvement resulted from reducing the amide hydrolysis side reaction.

Definitions

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denote optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl. The term "carboxylic acid" refers to a RC(O)OH compound where R can be hydrogen, or substituted or unsubstituted alkyl, alkenyl, alkynyl, aryl, substituted aryl. Exemplary carboxylic acids are formic acid, acetic acid, ethanoic acid, propionic acid, and the like.

The terms "halogen" or "halo" as used herein alone or as part of another group refer to chlorine, bromine, fluorine, and iodine.

The term "halide" refers to fluoride, chloride, bromide, or iodide ions.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics such as furyl, pyridyl, oxazolyl, pyrrolyl, indolyl, quinolinyl, or isoquinolinyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, acyl, acyloxy, nitro, amino, amido, nitro, cyano, ketals, acetals, esters and ethers.

The term "precious metal catalyst" refers to a solid metal catalyst in whatever form suitable and effective for achieving the hydrogenation reactions of the instant invention. Exemplary and preferred precious metal catalysts include platinum, palladium, ruthenium, osmium, iridium, rhodium, and the like, or mixtures thereof.

The following examples illustrate the invention.

EXAMPLES

Generally, a stirred Parr reactor was used for reactions under hydrogen, unless a Parr shaker is mentioned. The stirring speed was the same in all experiments and was estimated to be around 300 RPM.

Example 1

Conversion of Alpha-Hydroxy Zolpidem to Zolpidem Base

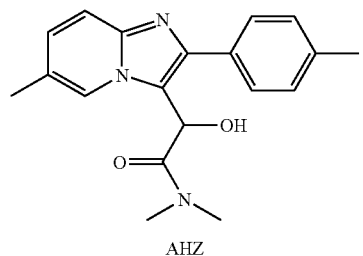

AHZ

Alpha hydroxy zolpidem (AHZ) was prepared by procedures similar to those in U.S. Pat. No. 4,794,185. Samples of this AHZ may have chloride ion in them, up to 0.5% by weight. The chloride ion has an effect on the reduction. Samples were washed with water until the chloride (as NaCl) concentration was as low as possible, in the region of 0.04% chloride by weight.

A solution of concentrated sulfuric acid (6.8 mL) diluted to 40 mL with glacial acetic acid was prepared (this was used for a number of experiments). A sample of low chloride AHZ, 1.50 g, was weighed out into the glass insert of a Parr stirred reactor (450 mL reactor volume). To this was added 37 mL of glacial acetic acid, followed by 3.0 mL of the sulfuric acid in acetic acid solution (containing 0.51 mL of concentrated sulfuric acid). The mixture was swirled until the solid dissolved. To this was added 25 µL of 1.4M LiBr in water. The mixture was swirled to assure mixing and to wash down any solid on the side of the glass. Then, 260 mg of 5% Pd/BaSO$_4$ catalyst (Engelhard) was added. The reactor was closed and placed in a heating mantle. Through the appropriate valves, the system was filled with nitrogen and vented several times. Hydrogen was added to a pressure of 10 PSI and vented, twice. The system was filled to a pressure of 20-25 PSI of hydrogen and the stirrer was started at a medium speed. The system was heated to 70° C. and controlled using a thermocouple. When the reaction had reached 60-70° C., the system was adjusted to a pressure of 35 PSI of hydrogen. It was closed off from further hydrogen in a reaction on this scale. The reaction was run for 21 hours. In general, a few hours after no hydrogen pressure change was sufficient for essentially complete reaction. The mixture was allowed to cool to 20-40° C. The reactor was vented, filled with nitrogen and vented several times. The mixture was poured into a beaker. A total of 6 mL of glacial acetic acid was used in rinsing and transferring the mixture from the reactor to the beaker. The mixture was filtered through a Whatman (fiberglass) microfibre filter. The filtrate was poured into 80 mL of ice-cooled water, with stirring. Ammonium hydroxide, approximately 50 mL, was added slowly, to a pH>8. The mixture was stirred ten minutes and filtered. The solid washed with water. This material was 98.2% zolpidem base by HPLC area purity. The yield was typically 90%.

Examples run by the above procedure are given in the table below. The reagents are all in the amounts described in Example 1, except for the bromide salt. Reagents of AR quality were used. The total amount of salt solution used is listed in the table. Products with purity of at least 69% were recrystallized from isopropanol, as in Example 1, to give zolpidem of >95% purity.

REDUCTIONS OF ALPHA-HYDROXY ZOLPIDEM TO ZOLPIDEM BASE

| Example | Aqueous Bromide salt solution | Yield, % | Area Percent zolpidem in HPLC | Area Percent AHZ in HPLC | Reaction time, h |
|---|---|---|---|---|---|
| 1 | 25 µL of 1.4M LiBr | 90 | 98.2 | 0.2 | 21 |
| 2 | 50 µL of 1.4M LiBr | 90 | 95.3 | 0.6 | 6 |
| 3 | 15 µL of 1.4M LiBr | 88 | 69.6 | 9.2 | 22 |
| 4 | 25 µL of 1.4M NaBr | 91 | 92.3 | 1.6 | 5 |
| 5 | 35 µL of 1.4M KBr | 91 | 98.5 | 0.4 | 6 |

Example 6

A solution of concentrated sulfuric acid (6.8 mL) diluted to 40 mL with glacial acetic acid was prepared. A sample of low chloride AHZ, 3.00 g, was weighed out. To this was added 37 mL of glacial acetic acid, followed by 6.0 mL of the sulfuric acid in acetic acid solution (contains 1.0 mL of concentrated sulfuric acid). The mixture was swirled until the solid dissolved. To the mixture was added 30 µL of 1.4M NaBr in water. The mixture was swirled to assure mixing and to wash down any solution on the side of the glass. Then, 267 mg of 5% Pd/BaSO$_4$ catalyst (Engelhard) was added. The reactor was closed and placed in a heating mantle. Through the appropriate valves, the system was filled with nitrogen and vented several times. Hydrogen was added to a pressure of 10 PSI and vented, twice. The system was filled to a pressure of 20-25 PSI of hydrogen and the stirrer was started at a medium speed. The system was heated to 70° C. and controlled using a thermocouple. When the reaction had reached 60-70° C., the system was adjusted to a pressure of 30-35 PSI of hydrogen. It was closed off from further hydrogen in a reaction on this scale. The reaction was run at 70° C. at least until there was no further pressure change, in this case 17 hours. After the reaction, the mixture was allowed to cool to 20-40° C. The reactor was vented, filled with nitrogen and vented several times. The mixture was poured into a beaker. A total of 8 mL of glacial acetic acid was used in rinsing and transferring the mixture from the reactor to the beaker. The mixture was filtered through a Whatman microfibre filter. The filtrate was poured into 100 mL of ice cooled water, with stirring. Ammonium hydroxide, 55 mL, was added slowly, to a pH>8. The mixture was stirred ten minutes and filtered. The solid washed with water. This material was 98.4% zolpidem base by HPLC area purity. The yield was 92%.

Example 7

A solution of concentrated sulfuric acid (6.8 mL) diluted to 40 mL with glacial acetic acid was prepared. A sample of low chloride AHZ, 4.50 g, was weighed out. To this was added 35 mL of glacial acetic acid, followed by 9.0 mL of the sulfuric acid in acetic acid solution (contains 1.5 mL of concentrated sulfuric acid). The mixture was swirled until the solid dissolved. To this was added 45 µL of 1.4M NaBr in water. The mixture was swirled to assure mixing and to wash down any solid on the side of the glass. Then, 400 mg of 5% Pd/BaSO$_4$ catalyst (Engelhard) was added. The reactor was closed and placed in a heating mantle. Through the appropriate valves, the system was filled with nitrogen and vented several times. Hydrogen was added to a pressure of 10 PSI and vented, twice. The system was filled to a pressure of 25 PSI of hydrogen and the stirrer was started at a medium speed. The system was heated to 70° C. and controlled using a thermocouple. When the reaction reached 60-70° C., the system was adjusted to a pressure of 35 PSI of hydrogen. It was closed off from further hydrogen in a reaction on this scale. The reaction was run at 70° C. for 6 hours. After the reaction, the mixture was allowed to cool to 20-40° C. with stirring. The reactor was vented, filled with nitrogen and vented several times. The mixture was poured into a beaker. A total of 10 mL of glacial acetic acid was used in rinsing and transferring. The mixture was filtered through a Whatman microfibre filter. The filtrate was poured into 130 mL of ice-cooled water with stirring. Ammonium hydroxide, 60 mL, was added slowly to a pH>8. The mixture was stirred ten minutes and filtered. The solid washed with water. This material was 88.9% zolpidem base by HPLC area purity, and contained some unreacted AHZ (4.8%). The yield was 97%.

Example 8

Recrystallization of Crude Zolpidem

Some samples were quite pure as a crude product, but some were only around 70% pure; both types were recrystallized from isopropanol.

A 5.9 g sample of crude zolpidem base of 73% purity (the impurities were mainly AHZ and AHZ-O-Acetate) was recrystallized from 40 mL of isopropanol, stirring it while allowing to cool. Filtration gave 2.7 g of zolpidem, 98.4% purity by HPLC area.

A 2.56 g sample of zolpidem base (95% purity) was recrystallized from 14 mL of isopropanol to give 2.02 g (80% recovery) of zolpidem, 97.6% purity.

A 14.4 g sample of zolpidem (97% purity by HPLC area) was recrystallized from 86 mL of isopropanol. The mixture was allowed to cool with stirring to room temperature and filtered. The filtrate was used to wash the remaining solid from the flask. The filter cake washed with 7 mL of isopropanol to give 10.3 g of a white solid, 99.2% zolpidem by HPLC area (254 nM UV detector).

Example 9

α-hydroxy-zolpidem-O-acetate

The O-Acetate of AHZ was produced along with the zolpidem product during the course of the above hydrogenations (Examples 1-7), and can be detected in the product in small amounts. Simply heating AHZ in glacial acetic acid with the typical amount of sulfuric acid present will convert most of it to the acetate in a few hours at 70° C. However, to obtain a clean sample for Example 10, the procedure below was followed.

A mixture of 3.00 g of AHZ, 1.50 mL of triethylamine, 15 mL of dichloromethane and 130 mg of 4-dimethylaminopyridine was stirred in an ice bath. Acetyl chloride, 0.75 mL was added and the mixture stirred overnight under nitrogen, letting the ice melt and the reaction come to room temperature. Then, 50 mL of dichloromethane was added followed by 5 mL of 1 M NaOH. The pH was >11. The mixture was separated and the dichloromethane dried with magnesium sulfate. The dichloromethane was evaporated and the residue stirred with 80 mL ethyl acetate. The ethyl acetate washed twice with 20 mL of water, dried over magnesium sulfate, evaporated and left under high vacuum for a few hours to give 2.6 g of the desired product. The NMR (300 MHZ, $CDCl_3$) shows aromatic peaks at δ values of 8.47 (broad, 1H), 7.56 (m, 3H), 7.28 (m, 2H), 6.83(s, 1H) as well as methyl peaks from 2.3-2.9 (15H total), with the acetate $CH_3$ at δ 2.3.

Example 10

Zolpidem

A 1.57 g sample of the O-acetate from Example 9 was dissolved in 37 mL of glacial acetic acid and to this was added 0.5 mL of sulfuric acid (3 mL of acetic acid solution) followed by 25 μL of 1.4 NaBr solution (aqueous) and 263 mg of 5% $Pd/BaSO_4$. The hydrogenation was run at a pressure of 30-40 PSI in the usual manner for 7 hours. Hydrogen was added, as needed, when the pressure was closer to 30 PSI. Work-up in the usual manner gave 1.13 g (86% yield). HPLC analysis indicated 74.4% zolpidem, 15.6% of starting material and 4.7% of AHZ. The crude product was recrystallized from isopropanol to give zolpidem.

Example 11

α-hydroxy-zolpidem-O-propionate

A mixture of 4.00 g of AHZ, 2.08 mL of triethylamine, 20 mL of dichloromethane and 185 mg of 4-dimethylaminopyridine was stirred in an ice bath. Propionyl chloride, 1.20 mL, was added and the mixture stirred overnight under nitrogen, letting the ice melt and the reaction come to room temperature. Then, 5 mL water was added followed by 0.5 mL of 1 M NaOH. The pH was 8.2. The mixture was separated and the dichloromethane solution concentrated on a rotary evaporator. The residue was stirred with 40 mL ethyl acetate and 15 mL of water. The ethyl acetate was separated, dried over magnesium sulfate and evaporated on a rotary evaporator to a solid. It was left under high vacuum for a few hours to give 4.2 g of the desired product.

NMR (300 MHZ, $CDCl_3$): δ 8.5(s, 1H), 7.5-7.6(m, 3H), 7.29(d, 1H), 7.13(dd, 1H), 2.81(s, 3H), 2.6(m, geminal coupling, 2H), 2.46(s, 3H), 2.40(s, 3H), 2.37(s, 3H), 1.27(t, 3H)

Example 12

Zolpidem

A 1.66 g sample of the O-propionate from Example 11 was dissolved in 40 mL of glacial acetic acid and to this was added 0.5 mL of sulfuric acid (3 mL of acetic acid solution) followed by 35 μL of 1.4M NaBr solution (aqueous) and 262 mg of 5% $Pd/BaSO_4$. The hydrogenation was run at a pressure of 30-40 PSI in the usual manner for 12.5 hours. Hydrogen was maintained at a pressure of 30-40 PSI by adding it from the cylinder periodically. Work-up in the usual manner gave 1.32 g (97% yield). HPLC analysis indicated 95.3% zolpidem, 0.8% of starting material and 1.0% of AHZ, as well as other peaks. The crude product was recrystallized from isopropanol to give zolpidem.

Example 13

Zolpidem

A solution of concentrated sulfuric acid (6.8 mL) diluted to 40 mL with glacial acetic acid was prepared. A sample of low chloride AHZ, 7.5 g, was weighed out. To this was added 30 mL of glacial acetic acid, followed by 15 mL of the sulfuric acid in acetic acid solution (contains 2.5 mL of concentrated sulfuric acid). The mixture was swirled until the solid dissolved. To this was added 54 μL of 1.4M NaBr in water. The mixture was swirled to assure mixing and to wash down any solid on the side of the glass. Then, 406 mg of 5% $Pd/BaSO_4$ catalyst (Engelhard) was added. The reactor was closed and placed in a heating mantle. Through the appropriate valves, the system was filled with nitrogen and vented several times. Hydrogen was added to a pressure of 10 PSI and vented, twice. The system was filled to a pressure of 25 PSI of hydrogen and the stirrer was started at a medium speed. The system was heated to 70° C. and controlled using a thermocouple. When the reaction has reached 60-70° C., the system was adjusted to a pressure of 37 PSI of hydrogen. The hydrogen valve was closed and hydrogen was added periodically to maintain a pressure of 30-40 PSI. The reaction was run at 70° C. for 14 hours. After the reaction, the mixture was allowed to cool to 31° C. with stirring. The reactor was vented, filled with nitrogen and vented several times. The mixture was poured into a beaker. A total of 10 mL of glacial acetic acid was used in rinsing and transferring the mixture from the reactor into the beaker. The mixture was filtered through a Whatman microfibre filter. The filtrate was poured into 150 mL of ice-cooled water, with stirring, followed by a rinse of the flask with 20 mL of water into the same. The pH was 1.1. During the pH adjustment, 50 mL of water was added to help stir the initially thick mixture. Ammonium hydroxide, 70 mL, was added slowly, to a pH>9. The mixture was stirred 20 minutes and filtered. The solid washed with water. This material was 98.3% zolpidem base by HPLC area purity. The yield was 87%.

Example 14

Zolpidem

A solution of concentrated sulfuric acid (6.8 mL) diluted to 40 mL with glacial acetic acid was prepared. A sample of low chloride AHZ, 9.0 g, was weighed out. To this was added 30 mL of glacial acetic acid, followed by 15 mL of the sulfuric acid in acetic acid solution (contained 2.5 mL of concentrated sulfuric acid). To this was added 65 μL of 1.4M NaBr in water. The mixture was swirled to assure mixing and to wash down any solid on the side of the glass. Then, 481 mg of 5% Pd/BaSO$_4$ catalyst (Engelhard) was added. The reactor was closed and placed in a heating mantle. Through the appropriate valves, the system was filled with nitrogen and vented several times. Hydrogen was added to a pressure of 10 PSI and vented, twice. The system was filled to a pressure of 25 PSI of hydrogen and the stirrer was started at a medium speed. The system was heated to 70° C. and controlled using a thermocouple. When the reaction has reached 70° C., the system was maintained at a pressure of 30-40 PSI of hydrogen. The reaction was run at 70° C. for 14 hours. After the reaction, the mixture was allowed to cool to 31° C. with stirring. The reactor was vented, filled with nitrogen and vented several times. The mixture was poured into a beaker. A total of 10 mL of glacial acetic acid was used in rinsing and transferring the mixture from the reactor to the beaker. The mixture was filtered through a Whatman microfibre filter. The rest of the work-up was as in example 13. The product, a 91% yield, was 95.0% pure by HPLC.

Example 15

Zolpidem

A solution of concentrated sulfuric acid (6.8 mL) diluted to 40 mL with glacial acetic acid was prepared. A sample of low chloride AHZ, 9.0 g, was weighed out. To this was added 30 mL of glacial acetic acid, followed by 18 mL of the sulfuric acid in acetic acid solution (contained 3.0 mL of concentrated sulfuric acid). To this was added 65 μL of 1.4M NaBr in water. The mixture was swirled to assure mixing and to wash down any solid on the side of the glass. Then, 483 mg of 5% Pd/BaSO$_4$ catalyst (Engelhard) was added. The reactor was closed and placed in a heating mantle. Through the appropriate valves, the system was filled with nitrogen and vented several times. Hydrogen was added to a pressure of 10 PSI and vented, twice. The system was filled to a pressure of 25 PSI of hydrogen and the stirrer was started at a medium speed. The system was heated to 70° C. and controlled using a thermocouple. When the reaction has reached 70° C., the system was maintained at a pressure of 30-40 PSI of hydrogen. The reaction was run at 70° C. for 14 hours. After the reaction, the mixture was allowed to cool to 31° C. with stirring. The reactor was vented, filled with nitrogen and vented several times. The mixture was poured into a beaker. A total of 10 mL of glacial acetic acid was used in rinsing and transferring the mixture from the reactor to the beaker. The mixture was filtered through a Whatman microfibre filter. The rest of the work-up was as in example 13. The product, a 91% yield, was 97.8% pure by HPLC.

Example 16

A 1.00 g sample of AHZ was dissolved in 25 mL of AcOH. Sulfuric acid, 0.34 mL, in acetic acid (1 mL of solution) was added, followed by 50 μL of 1.4M aqueous NaCl solution and 175 mg of 5% Pd/BaSO$_4$. Hydrogenation was run at 70° C. and a pressure of 20 PSI in a Parr Shaker apparatus for 4.5 hours. Filtration and aqueous work-up to a basic pH gave the crude product. HPLC of this indicated 36% of the product to be zolpidem.

Example 17

A 1.00 g sample of AHZ was dissolved in 25 mL of AcOH. Sulfuric acid, 0.34 mL, in acetic acid (1 mL of solution) was added, followed by 4.0 mg of choline chloride (Aldrich) and 170 mg of 5% Pd/BaSO$_4$. Hydrogenation was run at 70° C. and a pressure of 20-30 PSI in a Parr Shaker apparatus for four hours. Filtration and aqueous work-up to a basic pH gave the crude product, 0.87 g. HPLC of the crude product indicated 64% of the product to be zolpidem.

Example 18

A sample of AHZ, 1.50 g, was weighed out. To this was added 45 mL of glacial acetic acid, followed by 2.01 g of 70% ACS perchloric acid and 35 μL of 1.4M NaBr in water. The mixture was swirled to assure mixing and to wash down any solid on the side of the glass. Then, 260 mg of 5% Pd/BaSO$_4$ catalyst (Engelhard) was added. The reactor was closed and placed in a heating mantle. Through the appropriate valves, the system was filled with nitrogen and vented several times. Hydrogen was added and kept at a pressure of 15-20 PSI. The system was heated to 70° C. and controlled using a thermocouple. The reaction was run for 5 hours. Aqueous work-up with ammonia yielded a gum. Extraction with dichloromethane gave the crude product. HPLC indicated that 35% of the product was zolpidem base.

Example 19

A 1.00 g sample of AHZ was dissolved in 25 mL of AcOH. Sulfuric acid, 0.34 mL, in acetic acid (1 mL of solution) was added, followed by 25 μL of 0.95M aqueous NaF solution and 175 mg of 5% Pd/BaSO$_4$. Hydrogenation was run at 70° C. and a pressure of 20-30 PSI in a Parr Shaker apparatus for five hours. Filtration and aqueous work-up to a basic pH gave the crude product, a gum. HPLC of this indicated 29% of the product to be zolpidem. Also present were AHZ, 23%, and AHZ-O-Acetate, 34%.

Example 20

A 3.00 g sample of AHZ was dissolved in 40 mL of 96% formic acid. Sulfuric acid, 1.86 g, was added, followed by 30 μL of 1.4M aqueous NaBr solution and 268 mg of 5% Pd/BaSO4. The hydrogenation was run at 70° C. and a pressure of 30-40 PSI for 5 hours. The mixture was filtered and washed with 4 mL of formic acid. The filtrate was poured into 120 mL of water followed by a 20 mL water rinse. Ammonium hydroxide was added to a pH above 8. The mixture was extracted with 100 mL dichloromethane followed by 50 mL more dichloromethane. The dichloromethane was separated and evaporated to give an oil, which solidified to 2.59 g. HPLC analysis indicated 78% of zolpidem base and 18% of AHZ.

Example 21

Zolpidem from AHZ Sulfate

A 15.0 g sample of alpha-hydroxyzolpidem sulfate was suspended in 45 mL of glacial acetic acid in the glass insert of a Parr reactor. Concentrated sulfuric acid, 0.72 g, was added, followed by 58 μL of 4 M aqueous NaBr and 1.23 g of 5% Pd/BaSO4. Then 1.7 mL of acetic anhydride was added followed by 5 mL of glacial acetic acid to wash down the sides. The mixture was stirred at 500 RPM and heated to 87° C. Hydrogen pressure was kept at 20-30 psig for 5 hours. Filtration and work-up with water and isopropanol plus ammonium hydroxide to pH 9 gave 10.0 g of a solid after drying. HPLC indicated 98% of zolpidem base by area.

Example 22

A Parr pressure reactor equipped with a glass insert was charged with 1.2 g of wet (approximately 50%) 5% palladium on carbon catalyst, 30.5 g AHZ, 65 mL of acetic acid, 14.1 g 98% sulfuric acid, 0.15 mL of 4M aqueous sodium bromide and 7.0 g of acetic anhydride. The mixture was stirred at 500 RPM at 87.5° C. for six hours. After cooling, the catalyst was filtered from the mixture, and washed with 30 mL of distilled water. The filtrate and wash were combined. After combining, 90 mL of isopropyl alcohol and 30 milliliters of distilled water were added; aqueous ammonium hydroxide was added to adjust the pH to 9 (approximately 125 mL). The reaction mixture was cooled to 0-5° C. with stirring. The resulting solid was filtered and washed with 100 mL of distilled water. The solid was then dried at 90° C. and 25.6 g of zolpidem base was obtained; the yield was 88.6%.

Example 23

A pressure vessel was charged with AHZ, sulfuric acid, acetic anhydride, sodium bromide and palladium on carbon catalyst. The vessel was purged and pressurized with hydrogen to 30 psig. Subsequently, the vessel was heated to 80° C. for four hours, followed by cooling to room temperature (approximately 25° C.), venting the excess hydrogen gas and purging with nitrogen. The reaction mixture was filtered and washed with water. The filtrate and wash were combined and isopropyl alcohol was added followed by cooling to 0-5° C. After cooling, ammonium hydroxide was added to adjust the pH of the mixture to pH 9 making sure the temperature was below 40° C. The pH adjusted mixture was stirred and cooled to 5-15° C., followed by filtering and washing with water three times. The product was dried at 75° C.; the yield of zolpidem was 92%.

Example 24

Alpha-hydroxy zolpidem (1.35 kg), acetic acid (1.42 kg), 5% palladium on carbon (38.6 g), and sodium bromide solution (6.6 mL) were combined in a glass reactor and the reactor was closed. Sulfuric acid (0.625 kg) and acetic anhydride (0.31 kg) were added to the reactor with cooling to maintain the reaction temperature below 70° C. After the addition of the above reagents, the reactor was purged with nitrogen followed by addition of hydrogen gas to a pressure of 30 psig. The reaction mixture was heated to and maintained at 80-85° C., and the hydrogen pressure was maintained at 30 psig until the hydrogen uptake stopped. Typically, hydrogen uptake continued for about four hours. Once the reaction was complete, the reaction mixture was cooled to 20-30° C. and filtered to remove the catalyst. The filtered catalyst washed with 1 L of water and the wash water was added to the filtrate. 3 L of water and 3.15 kg of isopropyl alcohol were added to the filtrate, followed by addition of ammonium hydroxide (approximately 4.15 kg), with cooling to maintain the solution temperature at 20-40° C., to a final pH of 8.8-9.5. The slurry was cooled to 5-20° C. and stirred for 1 hour, filtered and washed with approximately 3 L of water. The resulting solid was dried at 75° C. The yield was 1 kg.

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

What is claimed is:
1. A process for the preparation of a heteroaryl acetamide from a heteroaryl α-hydroxyacetamide, the process comprising directly hydrogenating a heteroaryl α-hydroxyacetamide in the presence of hydrogen gas in a reaction mixture comprising a solvent system, the heteroaryl α-hydroxyacetamide, at least one strong acid, a halide and a precious metal catalyst, wherein the reaction mixture has a molar ratio of the starting heteroaryl α-hydroxyacetamide to water at the initiation of hydrogenolysis of at least about 2:1, the heteroaryl α-hydroxyacetamide corresponding to Formula 1 and the heteroaryl acetamide product corresponding to Formula 1A:

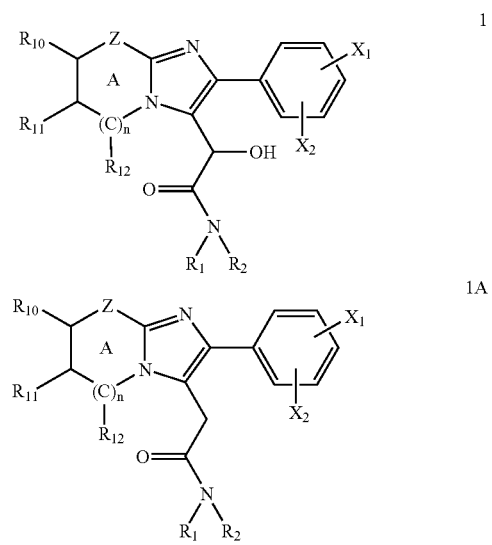

wherein
Z is O, $NR_{20}$ or $CR_{21}$;
$X_1$ and $X_2$ are independently selected from the group consisting of hydrogen, halogen, $C_{1-4}$ alkoxy, $C_{1-6}$ alkyl, —$CF_3$ and $CH_3SO_2$—;
$R_1$ and $R_2$ are independently hydrogen or hydrocarbyl;
$R_{10}$ is hydrogen, halogen, $C_{1-4}$ alkyl, or a member of a fused ring wherein the fused ring is (i) a substituted or unsubstituted, saturated or unsaturated, five or six-membered, heterocyclic or carbocyclic ring fused to the A ring comprising $R_{10}$, the carbon atom to which $R_{10}$ is attached, $R_{20}$, and the nitrogen atom to which $R_{20}$ is attached, or (ii) a six-membered, aromatic, carbocyclic ring fused to the A ring comprising $R_{10}$, $R_{11}$, and the carbon atoms to which $R_{10}$ and $R_{11}$ are attached, optionally substituted with Y at a substitutable position thereof;
$R_{11}$ is hydrogen, halogen, $C_{1-4}$ alkyl, or a member of a fused ring wherein the fused ring is (i) a six-membered, aromatic, carbocyclic ring fused to the A ring comprising $R_{10}$, $R_{11}$, and the carbon atoms to which $R_{10}$ and $R_{11}$ are attached, optionally substituted with Y at a substitutable position thereof, or (ii) a six-membered, aromatic, carbocyclic ring fused to the A ring comprising $R_{11}$, $R_{12}$, and the carbon atoms to which $R_{11}$ and $R_{12}$ are attached, optionally substituted with Y at a substitutable position thereof;
$R_{12}$, if present, is hydrogen, halogen, $C_{1-4}$ alkyl, or a member of a fused ring wherein the fused ring is (i) a six-membered, aromatic, carbocyclic ring fused to the A ring comprising $R_{11}$, $R_{12}$, and the carbon atoms to which $R_{11}$ and $R_{12}$ are attached, optionally substituted with Y at a substitutable position thereof;
$R_{20}$ is $C_{1-5}$ alkyl or a member of a fused ring wherein the fused ring is a substituted or unsubstituted, saturated or unsaturated, five or six-membered, heterocyclic or carbocyclic ring fused to the A ring comprising $R_{10}$, the carbon atom to which $R_{10}$ is attached, $R_{20}$, and the nitrogen atom to which $R_{20}$ is attached;

$R_{21}$ is hydrogen, halogen or $C_{1-4}$ alkyl;

n is 0 or 1;

each Y is independently hydrogen, halogen or $C_{1-4}$ alkyl; and when Z is $CR_{21}$, the A ring is aromatic.

2. The process of claim 1 wherein the heteroaryl α-hydroxyacetamide has the structure of Formula 7 and the heteroaryl acetamide has the structure of Formula 7A

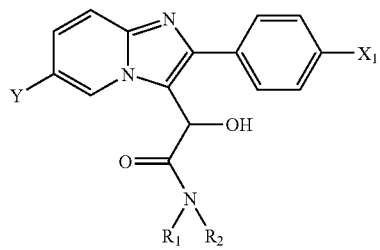

7

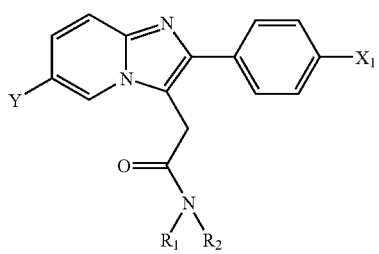

7A wherein

Y is $C_{1-4}$ alkyl;

$X_1$ is $C_{1-4}$ alkyl; and $R_1$ and $R_2$ are independently hydrogen or $C_{1-5}$ alkyl.

3. The process of claim 1 wherein the halide is bromide, the catalyst is palladium on carbon and the solvent system comprises acetic acid.

4. The process of claim 3 further comprising a water scavenger wherein the water scavenger is a carboxylic acid anhydride.

5. The process of claim 4 wherein the solvent system comprises acetic acid and the water scavenger is acetic anhydride.

6. The process of claim 5 wherein the heteroaryl α-hydroxyacetamide is α-hydroxyzolpidem and the heteroaryl acetamide is zolpidem.

7. A process for the preparation of a heteroaryl acetamide from a heteroaryl α-hydroxyacetamide, the process comprising forming a reaction mixture by combining a heteroaryl α-hydroxyacetamide, a strong acid, a halide, a precious metal catalyst and a water scavenger and contacting the reaction mixture with a hydrogen source, the heteroaryl α-hydroxyacetamide having the structure of Formula 1 and the heteroaryl acetamide having the structure of Formula 1A:

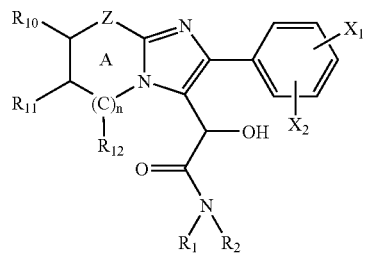

1

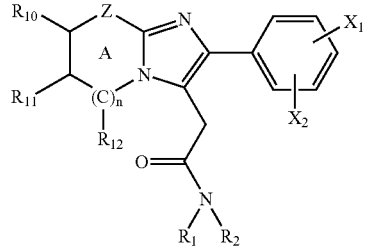

1A wherein

Z is O, $NR_{20}$ or $CR_{21}$;

$X_1$ and $X_2$ are independently selected from the group consisting of hydrogen, halogen, $C_{1-4}$ alkoxy, $C_{1-6}$ alkyl, —$CF_3$ and $CH_3SO_2$—;

$R_1$ and $R_2$ are independently hydrogen or hydrocarbyl;

$R_{10}$ is hydrogen, halogen, $C_{1-4}$ alkyl, or a member of a fused ring wherein the fused ring is (i) a substituted or unsubstituted, saturated or unsaturated, five or six-membered, heterocyclic or carbocyclic ring fused to the A ring comprising $R_{10}$, the carbon atom to which $R_{10}$ is attached, $R_{20}$, and the nitrogen atom to which $R_{20}$ is attached, or (ii) a six-membered, aromatic, carbocyclic ring fused to the A ring comprising $R_{10}$, $R_{11}$, and the carbon atoms to which $R_{10}$ and $R_{11}$ are attached, optionally substituted with Y at a substitutable position thereof;

$R_{11}$ is hydrogen, halogen, $C_{1-4}$ alkyl, or a member of a fused ring wherein the fused ring is (i) a six-membered, aromatic, carbocyclic ring fused to the A ring comprising $R_{10}$, $R_{11}$, and the carbon atoms to which $R_{10}$ and $R_{11}$ are attached, optionally substituted with Y at a substitutable position thereof, or (ii) a six-membered, aromatic, carbocyclic ring fused to the A ring comprising $R_{11}$, $R_{12}$, and the carbon atoms to which $R_{11}$ and $R_{12}$ are attached, optionally substituted with Y at a substitutable position thereof;

$R_{12}$, if present, is hydrogen, halogen, $C_{1-4}$ alkyl, or a member of a fused ring wherein the fused ring is (i) a six-membered, aromatic, carbocyclic ring fused to the A ring comprising $R_{11}$, $R_{12}$, and the carbon atoms to which $R_{11}$ and $R_{12}$ are attached, optionally substituted with Y at a substitutable position thereof;

$R_{20}$ is $C_{1-5}$ alkyl or a member of a fused ring wherein the fused ring is a substituted or unsubstituted, saturated or unsaturated, five or six-membered, heterocyclic or carbocyclic ring fused to the A ring comprising $R_{10}$, the carbon atom to which $R_{10}$ is attached, $R_{20}$, and the nitrogen atom to which $R_{20}$ is attached; $R_{21}$ is hydrogen, halogen or alkyl;

n is 0 or 1;

each Y is independently hydrogen, halogen or $C_{1-4}$ alkyl; and when Z is $CR_{21}$, the A ring is aromatic.

8. The process of claim 7 wherein the heteroaryl α-hydroxyacetamide has the structure of Formula 6 and the heteroaryl acetamide has the structure of Formula 6A

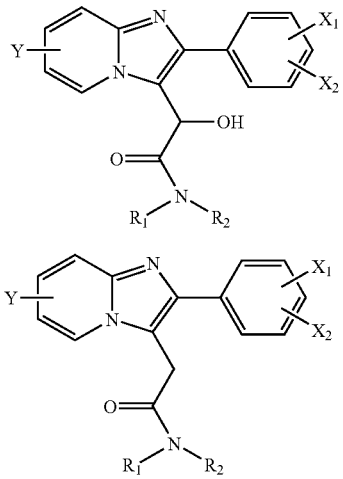

wherein

Y is hydrogen, halogen or $C_{1-4}$ alkyl;

$X_1$ and $X_2$ are independently selected from the group consisting of hydrogen, halogen, $C_{1-4}$ alkoxy, $C_{1-6}$alkyl, $CF_3$ and $CH_3SO_2$; and $R_1$ and $R_2$ are independently hydrogen or $C_{1-5}$ alkyl.

9. The process of claim 7 wherein more than 1.0 equivalent of the water scavenger per mole of water present in the reaction mixture is used to have excess water scavenger upon contact of the reaction mixture with the hydrogen source.

10. The process of claim 9 wherein the solvent system comprises a carboxylic acid and the water scavenger comprises the corresponding carboxylic acid anhydride.

11. The process of claim 10 wherein the heteroaryl α-hydroxyacetamide is α-hydroxyzolpidem and the heteroaryl acetamide is zolpidem.

12. The process of claim 11 wherein the strong acid is sulfuric acid, the halide is a bromide ion and the catalyst is palladium on carbon.

13. A process for the preparation of a heteroaryl acetamide from a heteroaryl α-hydroxyacetamide, the process comprising directly hydrogenating a heteroaryl α-hydroxyacetamide in the presence of hydrogen gas in a reaction mixture comprising a solvent system, the heteroaryl α-hydroxyacetamide, at least one strong acid, a halide and a palladium on carbon catalyst, wherein the reaction mixture contains less than about 2.5 wt. % water, the heteroaryl α-hydroxyacetamide corresponding to Formula 1 and the heteroaryl acetamide product corresponding to Formula 1A:

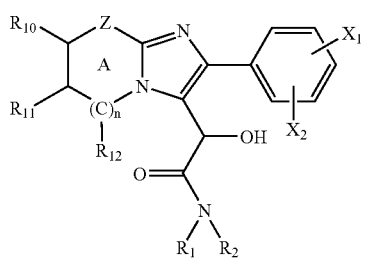

-continued

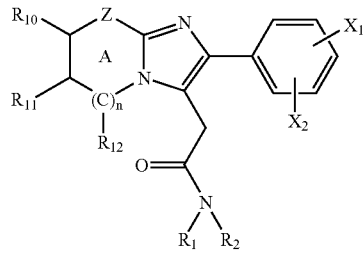

wherein

Z is O, $NR_{20}$ or $OR_{21}$;

$X_1$ and $X_2$ are independently selected from the group consisting of hydrogen, halogen, $C_{1-4}$ alkoxy, $C_{1-6}$ alkyl, $-CF_3$ and $CH_3SO_2-$;

$R_1$ and $R_2$ are independently hydrogen or hydrocarbyl;

$R_{10}$ is hydrogen, halogen, $C_{1-4}$ alkyl, or a member of a fused ring wherein the fused ring is (i) a substituted or unsubstituted, saturated or unsaturated, five or six-membered, heterocyclic or carbocyclic ring fused to the A ring comprising R10, the carbon atom to which R10 is attached, R20, and the nitrogen atom to which R20 is attached, or (ii) a six-membered, aromatic, carbocyclic ring fused to the A ring comprising $R_{10}$, $R_{11}$ and the carbon atoms to which $R_{10}$ and $R_{11}$ are attached, optionally substituted with Y at a substitutable position thereof;

$R_{11}$ is hydrogen, halogen, $C_{1-4}$ alkyl, or a member of a fused ring wherein the fused ring is (i) a six-membered, aromatic, carbocyclic ring fused to the A ring comprising $R_{10}$, $R_{11}$, and the carbon atoms to which $R_{10}$ and $R_{11}$ are attached, optionally substituted with Y at a substitutable position thereof, or (ii) a six-membered, aromatic, carbocyclic ring fused to the A ring comprising $R_{11}$, $R_{12}$, and the carbon atoms to which $R_{11}$ and $R_{12}$ are attached, optionally substituted with Y at a substitutable position thereof;

$R_{12}$, if present, is hydrogen, halogen, $C_{1-4}$ alkyl, or a member of a fused ring wherein the fused ring is (i) a six-membered, aromatic, carbocyclic ring fused to the A ring comprising $R_{11}$, $R_{12}$, and the carbon atoms to which $R_{11}$ and $R_{12}$ are attached, optionally substituted with Y at a substitutable position thereof;

$R_{20}$ is $C_{1-5}$ alkyl or a member of a fused ring wherein the fused ring is a substituted or unsubstituted, saturated or unsaturated, five or six-membered, heterocyclic or carbocyclic ring fused to the A ring comprising $R_{10}$, the carbon atom to which $R_{10}$ is attached, $R_{20}$, and the nitrogen atom to which $R_{20}$ is attached;

$R_1$ is hydrogen, halogen or $C_4$ alkyl;

n is 0 or 1;

each Y is independently hydrogen, halogen or $C_{1-4}$ alkyl; and when Z is $CR_{21}$, the A ring is aromatic.

14. The process of claim 13 wherein the heteroaryl α-hydroxyacetamide has the structure of Formula 6 and the heteroaryl acetamide has the structure of Formula 6A

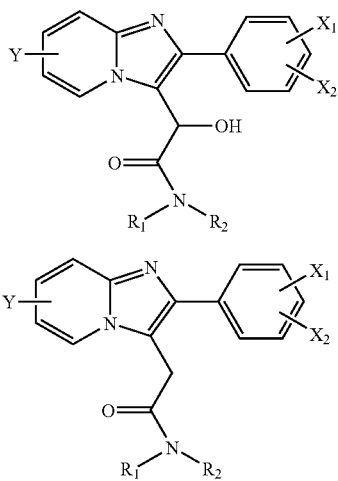

wherein
Y is hydrogen, halogen or $C_{1-4}$ alkyl;
$X_1$ and $X_4$ are independently selected from the group consisting of hydrogen, halogen, $C_{1-4}$ alkoxy, $C_{1-6}$ alkyl, $CF_3$ and $CH_3SO_2$—; and $R_1$ and $R_2$ are independently hydrogen or $C_{1-5}$ alkyl.

15. The process of claim 13 further comprising a water scavenger.

16. The process of claim 15 wherein the heteroaryl α-hydroxyacetamide is α-hydroxyzolpidem and the heteroaryl acetamide is zolpidem, the strong acid is sulfuric acid, the halide is a bromide ion, the solvent system comprises acetic acid and the water scavenger is acetic anhydride.

17. The process of claim 13 wherein the reaction mixture contains less than about 1.0 wt. % water at initiation of hydrogenation.

18. The process of claim 16 wherein the reaction mixture contains less than about 0.1 wt. % water at initiation of hydrogenation.

19. The process of claim 13 wherein the reaction mixture contains less than about 1.0 wt. % water during hydrogenation.

20. The process of claim 16 wherein the reaction mixture contains less than about 0.1 wt. % water during hydrogenation.

21. The process of claim 1 wherein reaction mixture has a halide concentration of less than about $2.1 \times 10^{-5}$ M.

22. The process of claim 7 wherein reaction mixture has a halide concentration of less than about $2.1 \times 10^{-5}$ M.

23. The process of claim 13 wherein reaction mixture has a halide concentration of less than about $2.1 \times 10^{-5}$ M.

* * * * *